United States Patent [19]

Auriol et al.

[11] Patent Number: 5,554,508

[45] Date of Patent: Sep. 10, 1996

[54] PROCESS FOR THE ENZYMATIC SYNTHESIS OF ALKYL ESTERS OF PEPTIDES AND PEPTIDES, AND MICROPARTICLES THEREFROM

[75] Inventors: Daniel H. Auriol; Francois B. Paul, both of Toulouse; Pierre F. Monsan, Mondonville, all of France

[73] Assignee: Ulice, Riom, France

[21] Appl. No.: 295,845

[22] PCT Filed: Mar. 2, 1993

[86] PCT No.: PCT/FR93/00213

§ 371 Date: Oct. 31, 1994

§ 102(e) Date: Oct. 31, 1994

[87] PCT Pub. No.: WO93/18180

PCT Pub. Date: Sep. 16, 1993

[30] Foreign Application Priority Data

Mar. 9, 1992 [FR] France .................... 92 02789

[51] Int. Cl.⁶ .............. C12P 21/06; C12P 7/62; A61K 9/16; A61K 38/01
[52] U.S. Cl. ............ 435/68.1; 435/135; 424/491; 514/2; 514/937
[58] Field of Search ............... 435/68.1, 135; 252/335, 354; 514/937, 2; 424/491

[56] References Cited

U.S. PATENT DOCUMENTS

| | | | |
|---|---|---|---|
| 4,826,818 | 5/1989 | Mori et al. | 514/21 |
| 5,021,248 | 6/1991 | Stark et al. | 426/96 |
| 5,145,702 | 9/1992 | Stark et al. | 426/531 |

FOREIGN PATENT DOCUMENTS 9003123  4/1990  WIPO.

OTHER PUBLICATIONS

Vidulac et al. (1983) *Tetrahedron*, 39(2), 269–274.
Morihara et al. (1987) *Trends in Biotechnol*, 5, 164–170.
Agricultural And Biological Chemistry, vol. 52, No. 3, 1988, pp. 855–856, H. Saito et al, "Papain-catalyzed Hydrolysis in an Aqueous Organic System".

*Primary Examiner*—David M. Naff
*Assistant Examiner*—Jon P. Weber
*Attorney, Agent, or Firm*—Antonelli, Terry, Stout & Kraus

[57] ABSTRACT

A process for the simultaneous enzymatic synthesis of a mixture of alkyl esters of peptides and peptides is presented. In the process, a protein substrate and at least one aliphatic alkanol having from 1 to 5 carbon atoms at a concentration of more than about 30% V/V, preferably 70% V/V to 90% V/V, are treated with a serine protease. A mixture of alkyl esters of peptides and peptides having an esterification value of at least 25% and an average molecular mass of about 3,000 to about 10,000 daltons is recovered. In a further step, the mixture of alkyl esters of peptides and peptides may be precipitated from an alcoholic medium, in an aqueous phase to prepare microparticles. The mixture of alkyl esters of peptides and peptides, or the microparticles may be used in cosmetic, food, pharmaceutical, wetting agent, film-agent, or emollient compositions.

51 Claims, No Drawings

PROCESS FOR THE ENZYMATIC SYNTHESIS OF ALKYL ESTERS OF PEPTIDES AND PEPTIDES, AND MICROPARTICLES THEREFROM

The present invention relates to a process for the enzymatic synthesis, called process for the enzymatic alcoholysis of proteins, which makes it possible to obtain peptide esters. The invention also relates to the products obtained by the process, as well as the use of these products as additives and ingredients in food, cosmetic and pharmaceutical and chemical products.

Because of their large quantity and their advantageous properties, proteins of animal origin (collagen, casein, gelatin and the like) and plant origin and their peptide derivatives constitute excellent raw materials for the chemical, food, pharmaceutical and cosmetic industries.

For example, International Patent Application WO-A-90/03123 describes the manufacture of microparticles of proteins intended to be used as fat substitutes in food products. Microparticles are manufactured by adding a solution of hydrophobic proteins, for example a prolamine, in alcoholic medium, to an aqueous medium. The protein is precipitated in the form of microparticles. Before being brought into contact with the aqueous medium, the protein may be subjected to an enzymatic hydrolysis. In this case, the microparticles consist of polypeptides having a molar mass of about 1000 daltons.

In the cosmetic field, peptide preparations are desired for their emulsifying power, their water-retaining power, their conditioning effect for shampoos and their emollient power. The peptides used have a molar mass which is most often less than 10,000 and rather less than 5000. They are generally obtained by the enzymatic route.

The use of proteins of plant origin in the cosmetic field is particularly desired.

For example, the use of peptides of gluten with a molar mass of less than 10,000, preferably of between 3000 and 5000, has been proposed because of their water-retaining power and their conditioning effect (JP-63253012). Such peptides are obtained by enzymatic hydrolysis with the aid of Alcalase, pepsin or acid protease from *Aspergillus niger*.

Peptide esters have also been proposed for cosmetic applications (JP-60097043, JP-60097042, JP-60084209). These peptide esters are obtained by condensing a peptide with a fatty or polyhydroxylated ester of an amino acid, catalyzed by a cysteine protease (EC 3.4.22).

Although the processes described up until now for the manufacture of protein derivatives are relatively efficient, they have nevertheless certain disadvantages. For example, microbial contamination of the reaction medium often poses a problem, the operating conditions favoring the growth of microorganisms. In addition, during a hydrolysis in aqueous medium, the molar mass of the product is difficult to control and the reaction often results in products with a molar mass less than that desired.

The process of the invention was therefore designed with the aim of developing an economical process which makes it possible to upgrade proteins of plant and animal origin, even in a crude state, for the manufacture of peptides and peptide esters, while minimizing the risk of microbial contamination of the medium.

The inventors have developed a process for the treatment of protein substrates which occurs in an alcoholic medium and which is catalyzed by an enzyme which is both proteolytic and esterolytic.

The esterase activity of certain enzymes known for their capacity to hydrolyze peptide bonds (peptide hydrolysates, EC 3.4.) is characterized by the possibility of catalyzing the hydrolysis of alkyl ester bonds of amino acids or of synthetic peptides present at low concentration in a buffered aqueous solution.

The inventors have observed that certain enzymes which possess both a protease and esterase activity lead to the synthesis of peptide esters when the substrate is a mixture of proteins or peptides present in an alcoholic medium and under certain conditions of pH. The enzyme uses alcohol in the place of water to cut the peptide bond between 2 amino acids of a protein or a peptide, or is capable of catalyzing the condensation of a peptide via its terminal carboxyl group with the alcohol according to a reaction which is the reverse of that observed during the hydrolysis of alkyl esters of peptides or of amino acids.

The enzymatic reaction where the substrate is a mixture of proteins or peptides and the co-substrate is alcohol is called alcoholysis reaction.

In alcoholic medium and under certain conditions of pH, the inventors observed the accumulation of peptide esters: the equilibrium between the reaction for the synthesis of esters (alcoholysis reaction) and the reaction for the hydrolysis of the said esters is pushed toward the synthesis reaction.

Under these conditions, the alcohol plays the role of substrate and solvent. In other words, the alcohol is responsible for the formation of esters and, at the same time, prevents their degradation.

A similar phenomenon has already been described by Vidaluc et al (Tetrahedron, vol. 39, No. 2, pp. 269–274, 1983). This article reports the synthesis of esters of amino acids from amino acids in alcoholic medium catalyzed by α-chymotrypsin. Having said this, the synthesis of peptide esters from complex protein substrates has not been described. Indeed, it is quite surprising that the synthesis reaction, catalyzed by the esterolytic enzyme and whose substrates are normally amino acids or small-sized peptides, can be carried out on a protein substrate composed of proteins and complex polypeptides.

The product obtained by the reaction of the invention is a mixture of peptides and peptide esters derived from simultaneous hydrolysis and alcoholysis reactions. The mixture has properties similar to those of 8the peptides derived from a conventional hydrolysis, but have a more marked hydrophobic character, which has a great advantage for many industrial applications.

The alcoholic medium makes it possible to reduce the risks of microbial contamination and, furthermore, to control the molar mass of the product. The alcoholic medium also ensures a good chemical stability of substrates such as glutamine, a predominant amino acid in plant proteins. The reaction is catalyzed by enzymes which are inexpensive and easy to obtain.

More particularly, the present invention relates to a process for the enzymatic synthesis of alkyl esters of peptides comprising the simultaneous bringing into contact of a protein substrate of animal or plant origin with, on the one hand, at least one enzyme having both a proteolytic activity and an esterolytic activity on proteins or on peptides and, on the other hand, with at least one alcohol, the said alcohol being either completely miscible with water, or at least partially soluble in water, characterized in that the simultaneous bringing into contact of the protein substrate, the enzyme and the alcohol is performed at a pH permitting the formation of alkyl esters of peptides.

The alcoholysis reaction occurs according to the following scheme:

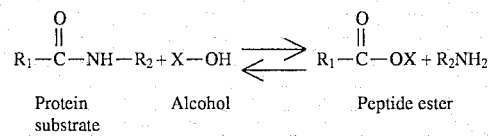

Protein substrate    Alcohol    Peptide ester

Within the context of the present invention, the expression "a protein substrate of animal or plant origin" means any source of proteins or polypeptides capable of playing the role of substrate for the proteolytic/esterolytic enzyme. As protein substrate of animal origin, gelatin or any gelatin-containing material is preferred.

As protein substrate of plant origin, there may be mentioned proteins derived from cereal grains such as wheat, maize, barley, oat, rice, rye, buckwheat, sorghum and triticale optionally in the form of whole grain, or grain fractions or any product derived from grinding the grain, such as flour or semolina. The products derived from grinding the grain are particularly preferred.

The protein substrate is not necessarily pure and can be used in the form of a complex mixture combined with non-protein materials. This is the case when the protein substrate consists of fractions or grain flour. It is also possible to use the protein fraction of the cereal grain, separated from the non-protein fraction. Wheat gluten is an example of this type of substrate. It is particularly preferred, according to the invention, to use as substrate the hydrophobic proteins known by the name of "prolamines", for example gliadin, zein, hordein and kafirin. These proteins are insoluble in water, but soluble in alcohol, and are a predominant constituent of cereal grains. Wheat gluten contains for example about 45% gliadin, and the protein fraction of maize contains about 60% zein.

The protein substrate for the alcoholysis reaction may also be a peptide or polypeptide material.

According to this variant of the invention, the peptide material may be obtained from a partial prehydrolysis of a protein material. In this case, the alcoholysis reaction is preceded by a partial hydrolysis step. The peptide esters are then obtained by condensing the peptides with the alcohol. The partial prehydrolysis can be carried out by the enzymatic, chemical or thermal route. The enzymatic route is preferred. For the partial hydrolysis process, it is advantageous to use the same proteolytic/esterolytic enzyme as that used subsequently in the alcoholysis reaction. The alcoholysis reaction can thus be initiated by simply adding alcohol and adjusting the pH to the values permitting the stable formation of esters. This permits easy control of the degree of hydrolysis and avoids total hydrolysis of the protein substrate. The peptide substrate normally has an average molar mass of about 4000 to 6000 Daltons. They are therefore medium-sized polypeptides.

In all cases, the substrate of the process has an average molar mass greater than 1000 Daltons.

The protein substrate may be soluble in water or soluble in alcohol. The alcoholysis reaction being carried out in an alcoholic medium, the use of an alcohol-insoluble protein such as gelatin gives rise to a heterogeneous reaction medium. When the substrate is a complex substrate such as gluten which is composed of various proteins of which about 50% are soluble in alcohol and 50% soluble in water, the reaction medium is multiphase.

According to the process of the invention, the protein substrate of animal or plant origin is brought into contact with at least one enzyme having a proteolytic and esterolytic activity on proteins or on peptides. The enzyme is preferably either a protease, or a carboxypeptidase. Serine or cysteine proteases exemplified by subtilisin (obtained from *Bacillus sp.*, preferably *Bacillus licheniformis*), or papain (obtained from pawpaw latex) respectively are particularly preferred. The double protease and esterase activity is not a property which all proteases possess. Having said this, by applying the test described below for detecting the formation of esters, a person skilled in the art can easily identify those which are suitable for the process of the invention. The enzyme may be in the form of an enzymatic preparation, for example in the form of a coarse enzyme mixture, such as a microbial culture supernatant, or may on the other hand be in purified form free of any other type of enzymatic activity and of any other contaminant. The enzymatic preparation may also be a mixture of proteases of various origins, provided that these various enzymes can function together.

Normally, the enzyme is used in free form, but it can also be immobilized on a solid support such as silica, or on beads or on membranes known in the art. The immobilization of the enzyme makes it possible to carry out the process of the invention continuously.

The operating conditions and especially the pH are critical, according to the process of the invention, for the efficiency of the alcoholysis reaction. The hydrolysis and alcoholysis reactions occur in parallel, but under certain conditions of pH, the esters do not accumulate in the reaction medium. There is however, a pH range in which the formation of esters is effective. The inventors have observed that, for the same enzyme, the optimum pH for the alcoholysis reaction is substantially lower than the optimum pH for the hydrolysis reaction as performed conventionally in an exclusively aqueous medium. For example, the optimum pH for the hydrolysis reaction using subtilisin is around pH 8 whereas the optimum pH for the alcoholysis reaction is around pH 5. Papain which has a pH optimum for the hydrolysis reaction of about 7 catalyzes the alcoholysis reaction between pH 5 and 7, particularly around pH 6. Generally, the pH should be acidic in order to allow the stable formation of esters. The bringing of the protein substrate into contact with subtilisin and the alcohol is carried out at pH 3 to 8, preferably at pH 4 to 6, for example about pH 5.

According to the method of the present invention, a person skilled in the art can without difficulty determine the pH at which the formation of peptide alkyl esters is obtained. It is sufficient to carry out the test for determining the quantity of alcohol bound to the product by basic hydrolysis of the ester group described in Example 1 below. This determination is carried out for a series of various pH values and the values which permit the formation of alkyl esters are thus determined. In the context of the present invention, the esterification value of the product which is considered as significant is at least about 10%. Preferably, the esterification value is at least 25% and advantageously at least 40%.

According to the process of the invention, the alcoholysis is carried out by bringing into contact, simultaneously, the protein substrate, the enzyme and an alcohol which is either completely miscible with water, or at least partially soluble in water. As examples of this type of alcohols, there may be mentioned aliphatic alkanols possessing between 1 and 5 carbon atoms, for example methanol, ethanol, propanol, butanol and pentanol. Those preferred are n-propanol, n-butanol and n-pentanol. The alcohols which are completely miscible, in all proportions, with water such as methanol, ethanol and n-propanol are particularly advantageous. However, when the alcohol is partially miscible or immiscible with water, the efficiency of the alcoholysis reaction can be increased by the presence of another compound which is both miscible with water and miscible with alcohol, for example 2-propanol.

The product obtained by the process of the invention is a mixture of peptides and peptide esters derived from simultaneous hydrolysis and alcoholysis reactions. The mixture consists of a heterogeneous population of peptides and peptide esters with variable chain lengths, the alkyl group of the esters being directly obtained from the alcohol, and therefore having between 1 and 5 carbon atoms. The precise nature of the product is influenced, on the one hand, by the nature of the substrate, and, on the other hand, by the purity of the enzyme. For example, a protein substrate composed of a mixture of various proteins will give rise to a highly complex mixture of esters and peptides. Likewise, a protease or a carboxypepsidase which is contaminated by other enzymes having other enzymatic activities might lead to the presence of other chemical substances in the product, especially if the substrate is also impure. The mixtures of peptides and peptide esters can be subjected to a purification step in order to obtain a mixture enriched with esters.

The solubility of the product in water or in alcohol varies according to the reagents and is not always the same as that of the substrate. For example, the use of wheat gliadin as substrate gives rise to esters which are soluble in water, whereas the use of maize zein leads to the formation of esters which are soluble in alcohol. Yet, gliadin and zein are both soluble in alcohol. When the protein substrate is a complex mixture of proteins having different solubilities, it is probable that the product of the alcoholysis reaction will consist of esters and peptides possessing different solubilities. In this case, the fraction which is soluble in water or soluble in alcohol can be recovered depending on the subsequent use of the product. For example, in the cosmetic field, water-soluble products are preferred.

The duration of the alcoholysis reaction varies between 2 to 30 hours according to the nature of the protein substrate and the alcohol. For example, the alcoholysis of a complex protein substrate such as gluten will occur preferably for about 24 hours. On the other hand, a pure protein substrate such as wheat gliadins will give rise, in a water-miscible alcoholic medium, to high esterification values after only 2 to 6 hours. The reaction is stopped by denaturation of the enzyme by adjusting the pH to a highly acidic value, optionally accompanied by heating at about 50° for 30 to 50 minutes.

The alcoholysis reaction normally occurs at a temperature of between 20° and 45° C., for example at around 25°.

The alcohol concentration is at least 30% v/v and preferably at least 70% v/v. When the alcohol is ethanol, the concentration may be 90% v/v. If the alcohol concentration is too low, the alcoholysis reaction cannot occur and the hydrolysis reaction predominates.

The average molar mass of the product can be determined by gel permeation chromatography (FPLC) and reflects the size of the peptides and the peptide esters obtained. The average molar mass of the product varies according to the nature of the protein substrate, that is to say protein or peptide, and according to the duration of the reaction and the concentration of the enzyme. In general, the average molar mass of the product derived from the alcoholysis of proteins is less than 10,000, for example between 6000 and 10,000, and that of the product derived from the alcoholysis of peptides is less than 5000, for example between 3000 and 5000. In all cases, the average molar mass of the product is greater than 1000 Daltons. The reaction of the invention therefore results in products having an average molar mass which is higher than the average molar mass obtained after a hydrolysis reaction in aqueous medium. Indeed, in alcoholic medium (n-propanol, 70% v/v), the average molar mass of the product of the gluten alcoholysis reaction, which is soluble in water, is 6200 (Example 1), whereas the product of the gluten hydrolysis reaction, which is soluble in water, is 4200 (Example 2). The condensing of maize peptides with n-propanol leads to the formation of a population of esterified peptides with an average molar mass of 4200.

According to a variant of the invention, the process may comprise an additional step which makes it possible to recover the product of the invention in the form of microparticles. According to this variant, the product should be soluble in alcoholic medium. Normally, this step comprises the precipitation of the product (soluble in alcoholic medium) in an aqueous phase. The aqueous phase advantageously contains at least one antiaggregating agent facilitating the formation of small-sized particles. As antiaggregating agents, there may be mentioned surface-active agents and gums such as gum arabic and carboxymethylcellulose. The antiaggregating agent is present in the aqueous phase at a concentration of between 0.2% and 1.0% (w/v). Microparticles should be understood in the context of the present invention as particles having a size of 0.2 to 10 μm, preferably around 1 μm, for example 0.8 to 1.2 μm. The introduction of the alcoholic solution into the aqueous solution is accompanied by vigorous stirring. Of course, it is important to ensure that the product is not denatured.

The product obtained by this embodiment of the invention is a stable aqueous dispersion of microparticles of peptides and peptide esters. They can be used for food, pharmaceutical and cosmetic applications. The use of the microparticles of the invention in the food industry as fat substitutes has proved particularly advantageous.

The properties of the product are in part dependent on the average molar mass. The operating conditions and the starting materials can therefore be chosen as a function of the subsequent use of the product.

For example, for a product intended to be used as a fat substitute, it is advantageous to carry out the alcoholysis reaction directly on the protein substrate without carrying out prior partial prehydrolysis.

The products of the invention have emulsifying and emollient properties and water-retaining power. These physical and chemical properties are advantageously exploited in cosmetic products as emulsifying agents, as film-forming agents, for example as conditioners in shampoos, as emollients, as thickening agents, as moisturizing agents, as washing and foaming base, or as any other additive or ingredient.

The products of the invention can also be used in the food or pharmaceutical industry as texturing additives or ingredients, as fat substitutes, as foaming agents or as emulsifying agents. It is in addition possible to use the products of the invention in chemical products, as wetting agents for example for washing products, as emulsifying agents, as emollient agents, as film-forming agents and as spinning agents.

Various embodiments of the invention will be illustrated by the following examples.

EXAMPLES

Example 1: Alcoholysis of Wheat Gluten Proteins

The vital wheat gluten used is marketed by the company Roquette (Lestrem, France).

300 g of gluten are dispersed in 1.2 l of 70% n-propanol v/v. The pH of the suspension is adjusted to 5.2 using 17 mmol of HCl. The food grade subtilisin (Alcalase® 2.4 L: subtilisin Carlsberg) is marketed by NOVO NORDISK® (Fontenay sous bois, France). 24 ml of subtilisin preparation are added to the suspension. The mixture is incubated for 24 hours with gentle stirring at 25° C.

The subtilisin is then denatured by adjusting the pH of the mixture to 3.5 with 115 mmol of HCl and heating at 50° C. for 40 minutes.

The n-propanol is removed by evaporation at 55° C. and the product suspended in water (volume of the aqueous suspension: 3.3 l, pH=3.1).

The pH of the aqueous suspension is adjusted to 6.0 with 113 mmol of NaOH. The soluble products are collected by centrifugation (5000 g, 15 min), microfiltered on a 0.2 micron filter and freeze-dried. The insoluble matter is removed.

After freeze-drying, the collected quantity of soluble product is 110 g.

Determination of the average molar mass of the product:

The average molar mass of the product is determined by gel permeation chromatography using a Pharmacia Superose 12 R HR 10/30® column (F.P.L.C.). The eluent is 50 mM sodium phosphate buffer, pH 7.0 containing 150 mM NaCl. The elution rate is 0.5 ml/min. The elution products are detected with the aid of a spectrophotometer whose absorption wavelength is fixed at 280 nm. The calibration of the column (correspondence molar mass/elution time) and the determination of the total volume are performed as indicated in the Pharmacia technical documentation.

The calibration line for the analytical system is obtained by expressing the decimal logarithm of the molar mass of calibration proteins as a function of the elution time or volume. The average molar mass of the water-soluble gluten product after alcoholysis reaction is calculated from the elution chromatogram with the aid of the formula:

$$\frac{\Sigma h_i M_i}{\Sigma h_i}$$

with, for an elution time or volume i:

$M_i$, the molar mass of the product eluted at the elution time or volume i on the calibration line, $h_i$, the height under the peak for an elution time or volume i.

The sample is prepared at a concentration of 5 g/l in the elution buffer and centrifuged if necessary.

Determination of the quantity of alcohol bound to the product by basic hydrolysis of the ester group:

The total alcohol contained in the sample corresponds to the alcohol bound to the product and optionally to the residual free alcohol not removed by evaporation or freeze-drying.

The alcohol bound to the product therefore corresponds to the total alcohol per gram of product minus the free alcohol per gram of product.

Total alcohol:

67 mg of product are introduced into an Eppendorf tube. 0.3 ml of water, then 0.3 ml of 2N NaOH are added and the tube is stoppered. The mixture is stirred and incubated at room temperature for 2 hours. The mixture is then acidified using 0.3 ml of 2.1N $H_2SO_4$. The mixture is centrifuged and the quantity of total alcohol per gram of product is determined by HPLC analysis of the centrifugation supernatant.

Free alcohol:

67 mg of product are introduced into an Eppendorf tube. 0.3 ml of water, then 0.6 ml of 10 mN $H_2SO_4$ are added and the tube is stoppered. The mixture is stirred, incubated at room temperature for 2 hours, centrifuged and the quantity of free alcohol per gram of product is determined as above.

The alcohol is analyzed by HPLC using a Polypore H column (Brownlee Labs, 250×7.0 mm, 10 microns). The eluent is a 10 mN aqueous $H_2SO_4$ solution at a flow rate of between 0.35 and 0.70 ml/min. The volume injected is 20 µl. The detector is a refractometer.

Esterification value:

The esterification value corresponds to the number of micromoles of alcohol bound per gram of product divided by the number of micromoles of peptides and peptide esters per gram of product.

Characterization of the product obtained by alcoholysis of gluten by subtilisin in the presence of 70% n-propanol v/v:

peptide content: 71% (Kjeldahl method)

average molar mass: 6200 n-propanol bound: 2.7 mg/g peptides esterification value: 28%

Example 2: Alcoholysis of Wheat Gluten Peptides

The wheat gluten peptides were prepared by hydrolyzing gluten with subtilisin (Alcalase) at pH=8: the average molar mass of the water-soluble peptides determined according to the conditions described in Example 1 is 4200.

75 g of gluten hydrolysate are dispersed in 0.75 l of 70% n-propanol v/v. The pH of the reaction medium is adjusted to 5.1 with 120 mmol of HCl. 15 ml of subtilisin (Alcase® 2.4 L) are added to the suspension. The mixture is incubated for 20 hours with gentle stirring at 25° C.

The subtilisin is then denatured by adjusting the pH of the mixture to 3.5 with 80 mmol of HCl and heating at 50° C. for 40 minutes. The n-propanol is removed by evaporation at 55° C. and the product suspended in water (volume of the aqueous suspension: 0.75 l, pH=2.9).

The pH of the aqueous suspension is adjusted to 6.0 with 85 mmol of NaOH. The soluble products are collected by centrifugation, microfiltered on a 0.2 micron filter and freeze-dried. The insoluble matter is removed. After freeze-drying, the collected quantity of soluble product is 61 g.

Characterization of the product obtained by alcoholysis of gluten peptides by subtilisin in the presence of 70% n-propanol v/v:

peptide content: 62% (Kjeldahl method)

average molar mass: 3900 n-propanol bound: 8.2 mg/g esterification value: 53%

Example 3: Alcoholysis of Gliadins in the Presence of Water-Miscible and -Immiscible Alcohols Reaction media containing:

gliadins (Sigma G-3375): 30 g/l subtilisin (Alcalase 2.4 L): 2% v/v alcohol: 70% were prepared at pH=5 (adjusted with HCl) and incubated at 25° C. with gentle stirring. After incubation, the subtilisin is denatured by adjusting the pH to 2 with HCl, the alcohol evaporated, the product suspended in water. The mixtures are then freeze-dried and the reaction products characterized.

TABLE 1

Alcoholysis of the gliadins in the presence of water-miscible and -immiscible alcohols:

| Alcohol 70% v/v | Duration of incubation h | Molar mass (products soluble at pH = 7.0 | Esterification value % (a) |
|---|---|---|---|
| Ethanol | 2 | 9900 | 79 |
| n-propanol | 6 | 8400 | 50 |
| n-butanol | 15 | 8100 | 15 |
| n-butanol: 45% 2-propanol: 25% | 15 | 8200 | 32 |
| n-pentanol | 15 | 4800 | 4 |
| n-pentanol 2-propanol | 15 | 8300 | 9 |

(a) The esterification value is given for the primary alcohol.

The efficiency of the alcoholysis reaction decreases when the aliphatic chain length increases (ethanol, propanol).

When the alcohol is partially miscible (n-butanol) or immiscible with water (n-pentanol), the efficiency of the alcoholysis reaction is increased by the presence of a third compound which is both miscible with water and miscible with alcohol (for example 2-propanol).

Example 4: Influence of the pH On the Efficiency of the Alcoholysis Reaction

Reaction media were prepared as detailed in Example 3 with only ethanol and n-propanol as alcohols used and the pH values of the reaction media adjusted to 5.0 or 7.0 with HCl. The products of the reaction after incubating for 6 hours were obtained as indicated in Example 3 and characterized (Table 2).

The hydrolysis of proteins with subtilisin is efficient at basic pH, 7 to 10. However, it was observed that the efficiency of the alcoholysis reaction is significantly increased when the pH of the reaction medium is acidic, the pH being adjusted to 5.0 in particular.

TABLE 2

Influence of the pH on the efficiency of the reaction for the alcoholysis of gliadins by subtilisin:

| Alcohol | pH synthesis medium | Mw | Esterification value % |
|---|---|---|---|
| Ethanol | 7.0 | 6700 | 14 |
| Ethanol | 5.0 | 9400 | 49 |
| N-propanol | 7.0 | 8300 | 39 |
| N-propanol | 5.0 | 8400 | 50 |

Example 5: Alcoholysis of Wheat Gluten Proteins By Papain 250 g of vital wheat gluten are dispersed in 1.0 l of 70% n-propanol v/v. The pH of the suspension is adjusted to 6.0 with HCl. 100 g of papain (6500 NF Gist Brocades, Seclin, France), and cystein (final concentration: 10 mM) are added to the suspension. The mixture is incubated for 24 hours with gentle stirring at 25° C. The product of the reaction is recovered as indicated in Example 1. The average molar mass of the soluble peptides at pH 6.0 is 5700 and the esterification value is equal to 9%.

Example 6: Alcoholysis of Gelatin by Subtilisin 25 g of food gelatin (140–160 bloom) are dispersed in 250 ml of 70% n-propanol v/v. The pH is adjusted to 5.0 with HCl (0.3 mmol). The subtilisin (2.5 ml of Alcalase 2.4 L) is added and the mixture is incubated for 22 hours with gentle stirring at 25° C. 12.5 ml of subtilisin preparation are then added and the mixture incubated for 4 hours. The subtilisin is finally denatured by adding 11 mmol of HCl (pH=3.5) and the mixture heated at 50° C. for 30 minutes. The alcohol is evaporated and the product diluted in water is freeze-dried. The average molar mass of the water-soluble products at pH=7 is 12,000 and the esterification value equal to 29%.

Example 7: Preparation of Microparticles from the Product of the Alcoholysis of Maize Zein by Subtilisin in the Presence of Ethanol 10 g of zein (total nitrogenous matter: 80.7% Sigma Z-3625) are solubilized in 100 ml of 90% v/v or 70% v/v ethanol. The mixtures are adjusted to pH 5 with HCl. The subtilisin (2 ml of Alcalase 2.4 L) is added and the mixtures are incubated for 48 hours at 25° C. The solutions are then filtered on paper and the microparticles are prepared according to the following procedure:

the alcoholic solution (100 ml) maintained at 40° C. is pumped at a rate of 4 ml/min into 0.8 l of an aqueous solution of gum arabic at 10 g/l maintained at 70° C. and vigorously stirred. The alcoholic solution comes into contact with the aqueous solution through a needle with a diameter of 0.8 mm plunging into the aqueous solution, the suspension of microparticles is incubated for at least 4 hours at 4° C. and filtered on paper, the alcohol contained in the filtrate is evaporated, the microparticles are obtained in suspension in water and dried by freeze-drying.

The characteristics of the products obtained are indicated in Table 3.

TABLE 3

Preparation of microparticles from the product of the alcoholysis of maize zein by subtilisin in the presence of ethanol:

| | | |
|---|---|---|
| Ethanol in the alcoholysis reaction, % v/v | 70 | 90 |
| T.N.M. in dry product, % | 55 | 54 |
| Yield of microparticulation of the T.N.M., % | 100 | 94 |
| Ethanol bound to the peptides mg/g peptides | 0.98 | 1.14 |

Example 8: Alcoholysis of Maize Peptides in the Presence of N-Propanol

The maize peptides were prepared according to the method of Example 2 and then subjected to an alcoholysis reaction. The medium and the reaction conditions were the following:

maize peptides: 100 g/l (molar mass: 5700)

n-propanol: 70% v/v

Alcalase: 2% v/v pH: 5.0 temperature: 25° C.

duration: 20 h

The product of the condensation reaction had the following characteristics:

molar mass: 4100 esterification value: 55%

We claim:

1. A process for the simultaneous enzymatic synthesis of a mixture of alkyl esters of peptides and peptides comprising:

simultaneously contacting a protein substrate of animal or plant origin with at least one serine protease having both a proteolytic activity and an esterolytic activity on proteins or peptides, and at least one aliphatic alkanol having from 1 to 5 carbon atoms, at a concentration of more than about 30% v/v, wherein the simultaneous contacting is performed at a pH of less than 7, and recovering a mixture of water soluble and/or alcohol soluble alkyl esters of peptides and peptides having an average molecular mass from about 3,000 to about 10,000 daltons, said mixture having an esterification value of at least 25%.

2. A process according to claim 1, wherein the protein substrate is a plant protein obtained from a cereal grain in the form of whole grain, or parts of grain or any product obtained by grinding the grain.

3. A process according to claim 2, wherein the cereal grain is selected from the group consisting of wheat, maize, barley, oat, rice, rye, buckwheat, sorghum and triticale.

4. A process according to claim 1, wherein the protein substrate comprises gelatin.

5. A process according to claim 1, wherein the protease is subtilisin.

6. A process according to claim 5, wherein the pH is between 4 and 6.

7. A process according to claim 1, wherein the enzyme is a carboxypeptidase.

8. A process according to claim 1, wherein the alcohol concentration is between 70% v/v and 90% v/v.

9. A process according to claim 1, wherein prior to the simultaneous contacting, the protein substrate is partially hydrolyzed.

10. A process according to claim 9, wherein the protein substrate is partially hydrolyzed to peptides by a protease.

11. A process according to claim 1, wherein microparticles are formed by precipitating the alcohol soluble recovered mixture of alkyl esters of peptides and peptides from an alcoholic medium, in an aqueous phase, and recovering the microparticles.

12. A mixture of peptides and alkyl esters of peptides obtained by the process according to claim 1.

13. A mixture according to claim 12, having an esterification value of at least 40%.

14. Microparticles obtained by the process according to claim 11.

15. Microparticles according to claim 14, having a size of between 0.2 and 10 μm.

16. A cosmetic product containing the microparticles of claim 14.

17. A cosmetic product containing the microparticles of claim 15.

18. A food product containing the microparticles of claim 14.

19. A food product containing the microparticles of claim 15.

20. A pharmaceutical composition containing the microparticles of claim 14.

21. A pharmaceutical composition containing the microparticles of claim 15.

22. A wetting agent comprising the microparticles of claim 14.

23. A wetting agent comprising the microparticles of claim 15.

24. An emulsifying agent comprising the microparticles of claim 14.

25. An emulsifying agent comprising the microparticles of claim 15.

26. An emollient agent comprising the microparticles of claim 14.

27. An emollient agent comprising the microparticles of claim 15.

28. A film-agent comprising the microparticles of claim 14.

29. A film-agent comprising the microparticles of claim 16.

30. A spinning agent comprising the microparticles of claim 14.

31. A spinning agent comprising the microparticles of claim 15.

32. A fat-substitute comprising the microparticles of claim 14.

33. A fat-substitute comprising the microparticles of claim 15.

34. A cosmetic product containing the mixture of claim 12.

35. A cosmetic product containing the mixture of claim 13.

36. A food product containing the mixture of claim 12.

37. A food product containing the mixture of claim 13.

38. A pharmaceutical composition containing the mixture of claim 12.

39. A pharmaceutical composition containing the mixture of claim 13.

40. A wetting agent comprising the mixture of claim 12.

41. A wetting agent comprising the mixture of claim 13.

42. An emulsifying agent comprising the mixture of claim 12.

43. An emulsifying agent comprising the mixture of claim 13.

44. An emollient agent comprising the mixture of claim 12.

45. An emollient agent comprising the mixture of claim 13.

46. A film-agent comprising the mixture of claim 12.

47. A film-agent comprising the mixture of claim 13.

48. A spinning agent comprising the mixture of claim 12.

49. A spinning agent comprising the mixture of claim 13.

50. A fat-substitute comprising the mixture of claim 12.

51. A fat-substitute comprising the mixture of claim 13.

* * * * *